United States Patent [19]

Klimisch et al.

[11] Patent Number: 5,008,101

[45] Date of Patent: Apr. 16, 1991

[54] SUNSCREEN FORMULATION CONTAINING A PHENYL FUNCTIONAL ORGANOSILICON COMPOUND

[75] Inventors: Helen M. Klimisch; Regina M. Malczewski, both of Midland County, Mich.

[73] Assignee: Dow Corning Corporation, Midland, Mich.

[21] Appl. No.: 446,267

[22] Filed: Dec. 5, 1989

[51] Int. Cl.$^5$ .......................... A61K 7/40; A61K 7/42; A61K 7/44

[52] U.S. Cl. ......................................... 424/59; 424/60

[58] Field of Search .................................... 424/59, 60

[56] References Cited

U.S. PATENT DOCUMENTS 2,714,115 7/1955 Holdstock ............................. 424/59
2,770,631 11/1956 Merker ................................. 424/59
2,833,802 5/1958 Merker .

Primary Examiner—Dale R. Ore
Attorney, Agent, or Firm—Jim L. DeCeasre

[57] ABSTRACT

A method of increasing the absorbance of ultraviolet light by sunscreen active compounds which are applied to a surface to protect the surface from excessive exposure to sunlight. A mixture is formed which includes at least one sunscreen active compound and an effective amount of a phenyl functional siloxane. The mixture is applied to the surface to be protected from excessive exposure to sunlight, and the surface including the mixture of the sunscreen active compound and the phenyl functional siloxane is exposed to light in the ultraviolet spectrum. A composition having increased absorbance of ultraviolet light for applying to a surface to protect the surface from excessive exposure to sunlight is also disclosed.

21 Claims, No Drawings

SUNSCREEN FORMULATION CONTAINING A PHENYL FUNCTIONAL ORGANOSILICON COMPOUND

BACKGROUND OF THE INVENTION

This invention relates to a sunscreen formulation which contains a phenyl functional organosilicon compound. More particularly the invention is directed to a sunscreen additive which functions to enhance the absorbance of ultraviolet light by sunscreen chemicals.

The sun emits energy in a continuous band throughout the electromagnetic spectrum. The shorter wavelengths are absorbed in the upper atmosphere. At sea level, the radiation is present in a range of about 290–400 nanometers. The production of sunburn termed "erythema" and the production of melanin pigment occurs at about 297 nanometers. About twenty minutes of exposure to midsummer sunlight is required to produce a minimum perceptible sunburn on normal Caucasian skin. Products which protect the skin from excessive exposure have become increasingly widespread in view of the advent of scientific data linking prolonged exposure to sunlight to aging effects on skin and the implications of skin cancer. Sunscreen products include physical screening agents such as titanium dioxide and zinc oxide which are opaque materials that block and scatter light, thus acting as mechanical barriers. Chemical sunscreening agents, however, are capable of absorbing ultraviolet light and offer selective protection against certain ultraviolet wave bands depending upon the absorption spectrum of the particular chemical sunscreening agent. Accordingly, a sunburn preventive agent is an active ingredient which absorbs ninety-five percent or more of light in the ultraviolet range of 290-320 nanometers. A suntanning agent is an active ingredient which absorbs up to about eighty-five percent of light in the ultraviolet range of 290-320 nanometers, but which transmits light at wavelengths in excess of about 320 nanometers. An opaque sunblocking agent is an active ingredient which reflects or scatters light in the ultraviolet and visible range at wavelengths of 290-770 nanometers.

Although most people are aware of the harmful effects of overexposure to the sun, modern lifestyles include significant amounts of outdoor activities such as golf, hiking, skiing, bicycling, jogging, and sun bathing. These activities do increase exposure to the sun but often result in a desirable tan and overall healthy appearance. Suntan lotions and oils therefore afford some degree of protection against premature wrinkles and painful burns while allowing the users to reap the benefits of sunshine while simultaneously preventing significant damage.

It has long been recognized that one deficiency of suntan products has been the failure of the product to protect against overexposure because the sunscreening agent in the product becomes diluted or is floated from the skin surface by contact with water or by the generation of perspiration. It has been found that resistance to water and perspiration can be imparted to a sunscreen formulation by incorporating therein water repellents or emollients. A significant number of compounds have therefore been devised for this purpose, among which are organosilicon compounds. Thus, it is well known to employ siloxanes in suntan lotions, sprays, creams, and stick products, for the purpose of providing a non-oily emolliency to the sunscreen formulation. These siloxane compounds also function as a non-sticky water barrier, improve spreadability, and provide the sunscreen formulation with a smooth and silky feel when it is applied. Such siloxane compounds are also known to be skin lubricants functioning to add lubricity and softness to the skin. For example, a suntan oil is disclosed in U.S. Pat. No. 4,857,304, issued Aug. 15, 1989. The suntan oil contains a fluorocarbon, a sunscreen active agent of isooctyl p-dimethylaminobenzoate, perfume, and a phenyl functional polysiloxane having a viscosity of fifteen centistokes measured at twenty-five degrees Centigrade. While the compositions of the present invention also include a phenyl functional siloxane, the primary function of the siloxanes of the present invention is to enhance the absorbance of the sunscreen active ingredient for ultraviolet light, rather than to provide water repellency, emolliency, spreadability, lubricity, and skin softening and lubricating characteristics to the formulation, as in the '304 patent. Thus, according to the present invention, certain phenyl functional siloxanes have been found which actually increase the ultraviolet light absorbing power of sunscreen active ingredients. Prior to the present invention, this function of enhancing sunscreen absorbance has been alleged for materials such as proteins, amino acid complexes, and aromatic compounds containing multiple rings. It is heretofore not known to employ phenyl functional siloxanes for such a sunscreen ultraviolet light absorbance enhancing function.

SUMMARY OF THE INVENTION

This invention is directed to a method of increasing the absorbance of ultraviolet light by sunscreen active compounds which are applied to a surface to protect the surface from excessive exposure to sunlight. The method includes the steps of forming a mixture which includes at least one sunscreen active compound and an effective amount of a phenyl functional siloxane, applying the mixture to the surface to be protected from excessive exposure to sunlight, and exposing the surface including the mixture of the sunscreen active compound and the phenyl functional siloxane to light in the ultraviolet spectrum.

The invention also relates to a composition having increased absorbance of ultraviolet light for applying to a surface to protect the surface from excessive exposure to sunlight. The composition includes a mixture of at least one sunscreen active compound, and an effective amount of a phenyl functional siloxane.

It is therefore an object of the present invention to provide an enhancer for sunscreen active compounds, and in which a mixture of the enhancer and the sunscreen active compound exhibits increased absorbance of ultraviolet light. As noted, the enhancer or potentiator is a phenyl functional siloxane.

These and other features, objects, and advantages, of the herein described present invention will be more clearly understood when considered in light of the following detailed description thereof.

DETAILED DESCRIPTION OF THE INVENTION

In accordance with the present invention, there is provided both a method and composition for enhancing the absorbance of ultraviolet light. An enhancer or potentiator is provided, and when the enhancer is mixed with a sunscreen active compound, the mixture exhibits an increased absorbance of ultraviolet light than would be exhibited by the sunscreen active compound in the absence of the potentiator. In fact, it is possible to achieve increases in sunscreen absorbance in excess of fifty fold, and upwards of one hundred fold, in accordance with the concept of the present invention. This is of significant advantage in that it is possible to provide increased skin protection while at the same time allowing for the use of lower amounts of the sunscreen active ingredient which often times is potentially irritating to skin tissue.

The enhancer compound is a phenyl functional siloxane, and for purposes of the present invention, the term "phenyl functional siloxane" is intended to include polyphenylmethylsiloxanes. Such compounds are well known and commercially available polymers having a generally linear structure. Useful polyphenylmethylsiloxanes include homopolymers of phenylmethylsiloxane units; copolymers of dimethylsiloxane and phenylmethylsiloxane units; copolymers of dimethylsiloxane and diphenylsiloxane units; and polymers containing dimethylsiloxane, phenylmethylsiloxane, and diphenylsiloxane units. Useful polyphenylmethylsiloxanes also include similar homopolymers and copolymers containing siloxane units having a phenyl and trimethylsilyloxy substituent on a silicon atom. Phenylmethylsiloxane polymers are generally terminated with triorganosiloxane units such as trimethylsiloxane, but may also be terminated by hydroxyl groups. While the siloxane compounds of the present invention are old in the art, their use in combination with sunscreen active ingredients to form mixtures exhibiting increased absorbance of ultraviolet light is new and believed to be novel and unobvious.

Preferably, the sunscreen active compound and the phenyl functional siloxane are present in the mixture in about equal amounts by weight, respectively. The mixture includes a solvent, and in a preferred embodiment of the present invention, the solvent is a volatile cyclic siloxane. This solvent is a cyclic siloxane having the formula $(CH_3)_2(SiO)_x$ wherein x is an integer from three to eight. In the most preferred embodiment of the present invention, the solvent is a cyclic siloxane having the formula $(CH_3)_2(SiO)_x$ wherein x is four or five, and including mixtures thereof. Such solvent compositions include, for example, octamethylcyclotetrasiloxane and decamethylcyclopentasiloxane. Such materials have viscosities of about five centistokes and less measured at twenty-five degrees Centigrade. These solvent materials provide to the mixture a non-cooling and non-stinging solvent like characteristic, and evaporate leaving little or no residue. Such materials are an alternative delivery vehicle suitable in instances where conventional materials such as alcohols, water, and mineral oil vehicles have been employed. The solvent can also be any aliphatic alcohol such as isopropyl alcohol or ethyl alcohol, esters such as isopropyl myristate and other volatile solvents such as ethyl acetate. It should be noted, however, that the solvent must be compatible with and capable of dissolving both the sunscreen active ingredient as well as the phenyl functional siloxane enhancer.

The phenyl functional siloxane has the formula selected from the group consisting of

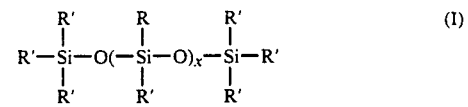

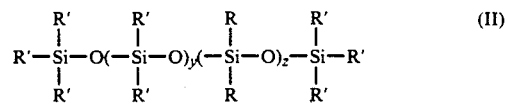

and

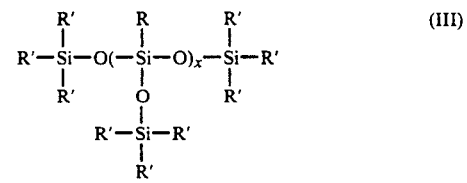

wherein R is a phenyl radical, R' is an alkyl radical having from one to seven carbon atoms, x is an integer of from one to one thousand, x and y are integers the sum of which is between two and one thousand. In a preferred embodiment of the present invention, the phenyl functional siloxane has a viscosity of about twenty to one hundred centistokes measured at twenty-five degrees Centigrade. In a more preferred embodiment of the present invention, the phenyl functional siloxane has a viscosity of about fifty centistokes measured at twenty-five degrees Centigrade. In the most preferred embodiment of the present invention, the phenyl functional siloxane has a viscosity of about twenty-two centistokes measured at twenty-five degrees Centigrade. However, phenyl functional siloxanes having viscosities ranging from about ten to about thirty thousand centistokes are appropriate in accordance with the present invention. The mixture is free of fluorocarbon compounds, and may also contain fragrances as well as other conventional sunscreen adjuvant ingredients known in the art.

It is intended that any sunscreen active compound be comprehended within the scope of the present invention. Sunscreens are evaluated according to their ability to slow the erythema or sunburn resulting from the exposure of skin to ultraviolet light between about 290-320 nanometers (the UV-B region). This is accomplished by absorbing damaging radiation before the radiation contacts the skin surface. Para-aminobenzoic acid derivatives and cinnamates such as octyl methoxycinnamate are two of the currently most preferable and commercially employed categories of sunscreen active compounds. UV-A region agents capable of absorbing ultraviolet light in the range of 320-400 nanometers are also useful in accordance with the present invention, including benzophenones and materials such as butyl methoxy dibenzoylmethane. Some additional examples of sunscreen chemicals which may be employed in accordance with the present invention are 2-ethoxyethyl p-methoxycinnamate; menthyl anthranilate; homomenthyl salicylate; glyceryl p-aminobenzoate; isobutyl p-aminobenzoate; isoamyl p-dimethylaminobenzoate; 2-hydroxy-4-methoxybenzophenone-5-sulfonic acid; 2,2'-dihydroxy-4-methoxybenzophenone; 2-hydroxy-4-methoxybenzophenone; 4-mono and 4-bis(3-hydroxypropyl)amino isomers of ethyl benzoate; and 2-ethylhexyl p-dimethylaminobenzoate.

The unexpected enhancement effect of phenyl functional siloxanes on UV-B category sunscreen active compounds was shown by the use of a thin sunscreen film of the mixture according to the present invention, applied to quartz slides. After applying the thin film of the mixture of the phenyl functional siloxane and the sunscreen active compound to the quartz slide, the quartz slide was subjected to spectrophotometric examination, for the purpose of determining the absorbance of the film. A series of slides were prepared including various combinations of sunscreen active compounds, phenyl functional siloxanes, and solvents. The results of the spectrophotometric measurements conducted on the several slides is shown in Table I. A control slide was employed for comparative purposes, containing as the enhancer a polydimethylsiloxane fluid having a viscosity of about two centistokes measured at twenty-five degrees Centigrade. Table I clearly indicates that enhancement values of the order of magnitude of from fifty to one hundred fold were obtained. Table I also clearly indicates that no enhancement was obtained when a mineral oil solvent was employed in combination with a sunscreen active compound and a phenyl functional siloxane in accordance with the present invention. The table also reveals that maximum enhancement is obtained employing about equal amounts of both the sunscreen active compound and the phenyl functional siloxane. Excessive quantities of enhancer did not result in improved or optimum ultraviolet light absorbance enhancement. The cyclic siloxane solvent provided the most consistent enhancement characteristics of the solvents tested. Following is an example which outlines a procedure illustrating the concept of the present invention.

EXAMPLE I

Into a glass vial was placed equal amounts of a sunscreen active compound, a phenyl functional siloxane enhancer, with the remainder being an appropriate solvent for the two ingredients. The ingredients were mixed until completely dissolved, and the mixture was painted onto previously cleaned quartz slides in the form of a thin film. The slides were weighed to insure that an equal distribution of the film was provided from slide to slide. The slides were placed in an oven and heated at about thirty-seven degrees Centigrade in order to simulate body temperature. The heating was continued for a period of time sufficient to achieve a constant weight, and the slides were cooled. The slides were placed in a UV spectrophotometer and the absorbance was scanned from 190–400 nanometers. The absorbance spectrum for each sample of the mixture was compared to the absorbance spectrum for the sunscreen active compound on a weight basis. The absorbance spectrum for the sunscreen active was obtained by following the above procedure using quartz slides containing thin films of the sunscreen active compound and the solvent, but without the phenyl functional siloxane. The fold enhancement of absorbance at the absorbance peak for the various slide samples was calculated and the results are indicated in Table I. The phenyl functional siloxanes used as the enhancer are shown in Table I by reference to the structural formula of the phenyl functional siloxane indicate previously as type (I) and (III).

TABLE I

| Sunscreen Chemical | Solvent | Silicone Enhancer | Wt. % Sunscreen | Wt. % Enhancer | Fold Enhancement |
|---|---|---|---|---|---|
| Escalol ® 507 | IPA | III | 5 | 5 | 18.5 |
| Escalol ® 507 | VS | III | 5 | 5 | 36.7 |
| Escalol ® 507 | VS | III | 5 | 5 | 60.4 |
| Escalol ® 507 | VS | III | 5 | 5 | 53 |
| Escalol ® 507 | VS | PDMS | 5 | 5 | 0 |
| Escalol ® 507 | VS | III | 2.5 | 2.5 | 11.5 |
| Escalol ® 507 | VS | III | 1 | 1 | 14 |
| Escalol ® 507 | VS | III | 1 | 5 | 20 |
| Escalol ® 507 | MO | III | 5 | 5 | 0 |
| Escalol ® 507 | VS | III | 5 | 5 | 28 |
| Escalol ® 507 | VS | I | 5 | 5 | 26 |
| PARSOL ® MCX | VS | III | 5 | 5 | 19 |
| PARSOL ® MCX | IPA | III | 5 | 5 | 56.9 |
| Sunarome ® Plus | VS | III | 5 | 5 | 25 |
| Sunarome ® Plus | VS | III | 5 | 5 | 36 |
| ARLATONE ® | VS | III | 5 | 5 | 76 |
| ARLATONE ® | VS | III | 5 | 5 | 100 |

IPA = Isopropyl alcohol.
VS = Volatile cyclic siloxane.
PDMS = Polydimethylsiloxane fluid, two centistokes.
MO = Mineral Oil.
Escalol ® = 2-ethylhexyl p-dimethylaminobenzoate, Van Dyk Company Inc., Belleville, N.J.
PARSOL ® = octylmethoxy cinnamate, Givaudan Corporation, Clifton, N.J.
ARLATONE ® = 2-ethylhexyl p-dimethylaminobenzoate, ICI Americas, Inc., Wilmington, Delaware It will be apparent from the foregoing that many other variations and modifications may be made in the compounds, compositions, structures, and methods, described herein, without departing substantially from the essential features and concepts of the present invention. Accordingly, it should be clearly understood that the forms of the invention described herein are exemplary only and are not intended as limitations on the scope of the present invention as defined in the appended claims.

That which is claimed is:

1. A method of increasing the absorbance of ultraviolet light by ultraviolet light absorbing sunscreen compounds which are applied to skin to protect the skin from excessive exposure to sunlight comprising forming a mixture which includes at least one sunscreen compound and an effective amount of a phenyl functional siloxane, applying the mixture to the skin to be protected from excessive exposure to sunlight, and exposing the skin including the mixture of the sunscreen compound and the phenyl functional siloxane to light in the ultraviolet spectrum, the phenyl functional siloxane having the formula selected from the group consisting of

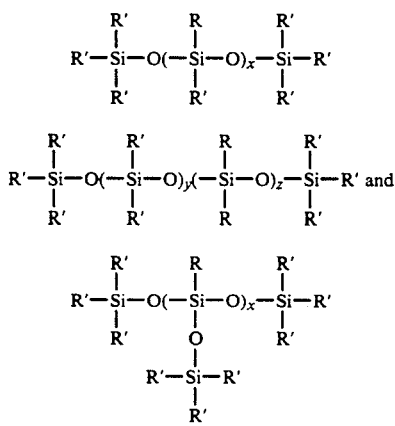

wherein R is a phenyl radical, R' is an alkyl radical having from one to seven carbon atoms, x is an integer of from one to one thousand, x and y are integers the sum of which is between two and one thousand.

2. The method of claim 1 in which the sunscreen compound and the phenyl functional siloxane are present in the mixture in about equal amounts by weight respectively.

3. The method of claim 1 in which the mixture includes a cyclic siloxane having the formula $(CH_3)_2(SiO)_x$ wherein x is an integer from three to eight.

4. The method of claim 1 in which the sunscreen compound is selected from the group consisting of para-aminobenzoic acid derivatives, benzophenones, and cinnamates.

5. The method of claim 1 in which the sunscreen compound is selected from the group consisting of octyl methoxycinnamate, butyl methoxy dibenzoylmethane, 2-ethoxyethyl p-methoxycinnamate, menthyl anthranilate, homomenthyl, salicylate, glyceryl p-aminobenzoate, isobutyl p-aminobenzoate, isoamyl p-dimethylaminobenzoate, 2-hydroxy-4-methoxybenzophenone-5-sulfonic acid, 2,2'-dihydroxy-4-methoxybenzophenone, 2-hydroxy-4-methoxybenzophenone, 4-mono and 4-bis(3-hydroxypropyl)amino isomers of ethyl benzoate, and 2-ethylhexyl p-dimethylaminobenzoate.

6. The method of claim 1 in which the mixture includes a compound selected from the group consisting of isopropyl alcohol, ethyl alcohol, isopropyl myristate, and ethyl acetate.

7. A method of increasing the absorbance of ultraviolet light by ultraviolet light absorbing sunscreen compounds which are applied to skin to protect the skin from excessive exposure to sunlight comprising forming a mixture which includes at least one sunscreen compound and an effective amount of a phenyl functional siloxane, applying the mixture to the skin to be protected from excessive exposure to sunlight, and exposing the skin including the mixture of the sunscreen compound and the phenyl functional siloxane to light in the ultraviolet spectrum, the sunscreen compound and the phenyl functional siloxane being present in the mixture in about equal amounts by weight respectively, the mixture including a cyclic siloxane having the formula $(CH_3)_2(SiO)_x$ wherein x is an integer from three to eight, the phenyl functional siloxane having the formula

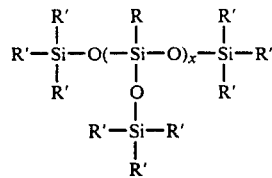

wherein R is a phenyl radical, R' is an alkyl radical having from one to seven carbon atoms, and x is an integer of from one to one thousand.

8. The method of claim 7 in which the sunscreen compound is selected from the group consisting of para-aminobenzoic acid derivatives, benzophenones, and cinnamates.

9. The method of claim 7 in which the sunscreen compound is selected from the group consisting of octyl methoxycinnamate, butyl methoxy dibenzoylmethane, 2-ethoxyethyl p-methoxycinnamate, menthyl anthranilate, homomenthyl salicylate, glyceryl p-aminobenzoate, isobutyl p-aminobenzoate, isoamyl p-dimethylaminobenzoate, 2-hydroxy-4-methoxybenzophenone-5-sulfonic acid, 2,2-dihydroxy-4-methoxybenzophenone, 2-hydroxy-4-methoxybenzophenone, 4-mono and 4-bis(3-hydroxypropyl)amino isomers of ethyl benzoate, and 2-ethylhexyl p-dimethylaminobenzoate.

10. A composition having increased absorbance of ultraviolet light for applying to skin to protect the skin from excessive exposure to sunlight comprising a mixture which includes at least one ultraviolet light absorbing compound, and an effective amount of a phenyl functional siloxane, the phenyl functional siloxane having the formula selected from the group consisting of

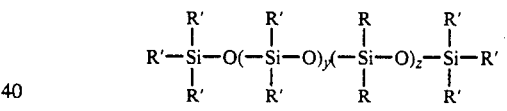

and

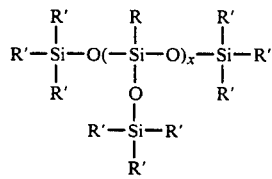

wherein R is a phenyl radical, R' is an alkyl radical having from one to seven carbon atoms, x is an integer of from one to one thousand, x and y are integers the sum of which is between two and one thousand.

11. The composition of claim 10 in which the sunscreen active compound and the phenyl functional siloxane are present in the mixture in about equal amounts by weight respectfully.

12. The composition of claim 10 in which the mixture includes a cyclic siloxane having the formula $(CH_3)_2(SiO)_x$ wherein x is an integer from three to eight.

13. The composition of claim 10 in which the sunscreen compound is selected from the group consisting of para-aminobenzoic acid derivatives, benzophenones, and cinnamates.

14. The composition of claim 10 in which the sunscreen compound is selected from the group consisting of octyl methoxycinnamate, butyl methoxy dibenzoylmethane, 2-ethoxyethyl p-methoxycinnamate, menthyl anthranilate, homomenthyl salicylate, glyceryl p-aminobenzoate, isobutyl p-aminobenzoate, isoamyl p-dimethylaminobenzoate, 2-hydroxy-4-methoxybenzophenone-5-sulfonic acid, 2,2-dihydroxy-4-methoxybenzophenone, 2-hydroxy-4-methoxybenzophenone, 4-mono and 4-bis(3-hydroxypropyl)amino isomers of ethyl benzoate, and 2-ethylhexyl p-dimethylaminobenzoate.

15. The composition of claim 10 in which the mixture includes a compound selected from the group consisting of isopropyl alcohol, ethyl alcohol, isopropyl myristate, and ethyl acetate.

16. A composition having increased absorbance of ultraviolet light for applying to skin in the form of a film comprising a mixture which includes at least one ultraviolet light absorbing compound, and an effective amount of phenyl functional siloxane, the phenyl functional siloxane having the formula selected from the group consisting of

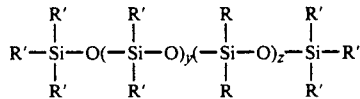

and

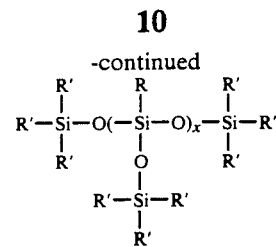

wherein R is a phenyl radical, R' is an alkyl radical having from one to seven carbon atoms, x is an integer of from one to one thousand, x and y are integers the sum of which is between two and one thousand.

17. The composition of claim 16 in which the light absorbing compound and the phenyl functional siloxane are present in the mixture in about equal amounts by weight respectively.

18. The composition of claim 16 in which the mixture includes a cyclic siloxane having the formula $(CH_3)_2(SiO)_x$ wherein x is an integer from three to eight.

19. The composition of claim 16 in which the light absorbing compound is selected from the group consisting of para-aminobenzoic acid derivatives, benzophenones, and cinnamates.

20. The composition of claim 16 in which the light absorbing compound is selected from the group consisting of octyl methoxycinnamate, butyl methoxy dibenzoylmethane, 2-ethoxyethyl p-methoxycinnamate, menthyl anthranilate, homomenthyl salicylate, glyceryl p-aminobenzoate, isobutyl p-aminobenzoate, isoamyl p-dimethylaminobenzoate, 2-hydroxy-4-methoxybenzophenone-5-sulfonic acid, 2,2-dihydroxy-4-methoxybenzophenone, 2-hydroxy-4-methoxybenzophenone, 4-mono and 4-bis(3-hydroxypropyl)amino isomers of ethyl benzoate, and 2-ethylhexyl p-dimethylaminobenzoate.

21. The composition of claim 16 in which the mixture includes a compound selected from the group consisting of isopropyl alcohol, ethyl alcohol, isopropyl myristate, and ethyl acetate.

* * * * *

UNITED STATES PATENT AND TRADEMARK OFFICE
CERTIFICATE OF CORRECTION

PATENT NO. : 5,008,101

DATED : April 16, 1991

INVENTOR(S) : Helen Klimisch and Regina Malczewski

It is certified that error appears in the above-identified patent and that said Letters Patent is hereby corrected as shown below:

In Column 4, line 22; Column 7, line 23; Column 8, line 53; and Column 10, line 12; the phrase "x and y" should read ---y and z---.

Signed and Sealed this

Twenty-second Day of September, 1992

Attest:

DOUGLAS B. COMER

Attesting Officer     Acting Commissioner of Patents and Trademarks